US011761864B2

United States Patent
Alruwaili et al.

(10) Patent No.: US 11,761,864 B2
(45) Date of Patent: Sep. 19, 2023

(54) THICK-WALL CYLINDER EXPERIMENT SETUP FOR WELLBORE STABILITY ANALYSIS

(71) Applicant: SAUDI ARABIAN OIL COMPANY, Dhahran (SA)

(72) Inventors: Khalid M. Alruwaili, Dammam (SA); Yanhui Han, Houston, TX (US); Murtadha J. AlTammar, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 17/644,832

(22) Filed: Dec. 17, 2021

(65) Prior Publication Data
US 2023/0194400 A1 Jun. 22, 2023

(51) Int. Cl.
*G01N 3/08* (2006.01)
*G01N 33/24* (2006.01)
*G01N 1/28* (2006.01)

(52) U.S. Cl.
CPC ............... *G01N 3/08* (2013.01); *G01N 1/286* (2013.01); *G01N 33/24* (2013.01);
(Continued)

(58) Field of Classification Search
CPC .......... G01N 3/08; G01N 1/286; G01N 33/24; G01N 2203/0019; G01N 2203/006;
(Continued)

(56) References Cited

U.S. PATENT DOCUMENTS

| 4,573,342 | A | * | 3/1986 | Jones ..................... G01N 15/08 73/38 |
| 5,345,819 | A | | 9/1994 | Dearing, Jr. |
| 10,845,354 | B2 | * | 11/2020 | Hugghins ............. E21B 49/005 |

FOREIGN PATENT DOCUMENTS

| CN | 101509852 A | 8/2009 |
| CN | 203465174 U | 3/2014 |

(Continued)

OTHER PUBLICATIONS

W. J. Winters et al. "The 1987 IADC fixed cutter bit classification system" In SPE/IADC drilling conference. Society of Petroleum Engineers; Jan. 1987 (11 pages).
(Continued)

*Primary Examiner* — Ryan D Walsh
(74) *Attorney, Agent, or Firm* — Osha Bergman Watanabe & Burton LLP

(57) ABSTRACT

A method includes preparing a rocklike core sample for compressive testing, the rocklike core sample defining a longitudinal axis and having first and second axial ends. Preparing the rocklike core sample includes providing a throughhole in the rocklike core sample, the throughhole extending between a first opening at the first axial end and a second opening at the second axial end, wherein the first opening and the second opening are dimensioned differently. The rocklike core sample is mounted in a compressive testing apparatus, and a compressive test is performed on the rocklike core sample in the compressive testing apparatus. The compressive test includes compression in axial and radial directions. A related system includes a compressive testing apparatus and a sample preparation apparatus which prepares a rocklike core sample for compressive testing in the compressive testing apparatus, via providing a throughhole in the rocklike core sample.

20 Claims, 6 Drawing Sheets

(52) U.S. Cl.
CPC .................. *G01N 2203/006* (2013.01); *G01N 2203/0019* (2013.01); *G01N 2203/0085* (2013.01); *G01N 2203/027* (2013.01); *G01N 2203/0256* (2013.01); *G01N 2203/0266* (2013.01)

(58) Field of Classification Search
CPC ... G01N 2203/0085; G01N 2203/0256; G01N 2203/0266; G01N 2203/027
See application file for complete search history.

(56) References Cited

FOREIGN PATENT DOCUMENTS

| | | | | |
|---|---|---|---|---|
| CN | 109540766 A | * | 3/2019 | |
| CN | 107505207 B | | 12/2019 | |
| CN | 210768587 U | | 6/2020 | |
| CN | 110018056 B | | 9/2020 | |
| CN | 111827987 A | | 10/2020 | |
| CN | 112362441 A | * | 2/2021 | ............. G01N 1/286 |
| CN | 111982623 B | | 3/2021 | |
| CN | 112858022 A | | 5/2021 | |
| CN | 112903504 A | | 6/2021 | |
| CN | 113216927 A | | 8/2021 | |
| CN | 113219000 A | | 8/2021 | |
| JP | 3852043 B2 | | 11/2006 | |
| WO | WO-2007035946 A2 | * | 3/2007 | ............... G01N 3/24 |

OTHER PUBLICATIONS

J. F. Brett et al. "Bit whirl—a new theory of PDC bit failure" SPE Drilling Engineering, 5(04); 1990 (7 pages).

J. Tronvoll et al. "Perforation Cavity Stability: Com pre hensive Laboratory Experiments and Numerical Analysis" Society of Petroleum Engineers, SPE 24799; Jan. 1992 (11 pages).

International Search Report and Written Opinion issued in Application No. PCT/US2022/053185, dated Apr. 18, 2023 (21 pages).

P. Zhuang et al.; "Loading and unloading of a thick-walled cylinder of critical-state soils: large strain analysis with applications", Acta Geotechnica; vol. 16; No. 1; Jun. 4, 2020; pp. 237-261 (25 pages).

V. Fattahpour et al.; "An experimental investigation on the effect of rock strength and perforation size on sand production", Journal of Petroleum Science and Engineering; vol. 86; Mar. 14, 2012; pp. 172-189 (18 pages).

"Wikipedia—Core Sample", Oct. 19, 2021; pp. 1-5; Retrieved from the Internet Apr. 4, 2023: URL: https://web.archive.org/web/20211107095356/https://en.wikipedia.org/wiki/Core_Sample (5 pages).

* cited by examiner

THICK-WALL CYLINDER EXPERIMENT SETUP FOR WELLBORE STABILITY ANALYSIS

BACKGROUND

Conventionally, thick wall cylinder (TWC) tests simulate actual loading conditions of rock under downhole stresses, that may be found in a subsurface layer at a well site. This normally involves providing a rock sample that is cylindrical in shape and loaded in a triaxial load frame, with compressive loads then applied from axial and radial directions. This helps determine a measure of pressures downhole that may lead to contingencies such as sand production or casing collapse. However, it has often been found that conventional tests are still not fully adequate for helping simulate downhole conditions.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method including preparing a rocklike core sample for compressive testing, the rocklike core sample defining a longitudinal axis and having first and second axial ends. Preparing the rocklike core sample includes providing a throughhole in the rocklike core sample, the throughhole extending between a first opening at the first axial end and a second opening at the second axial end, wherein the first opening and the second opening are dimensioned differently. The rocklike core sample is mounted in a compressive testing apparatus, and a compressive test is performed on the rocklike core sample in the compressive testing apparatus. The compressive test includes compression in an axial direction parallel to the longitudinal axis and in a radial direction with respect to the longitudinal axis.

In one aspect, embodiments disclosed herein relate to a system including a compressive testing apparatus and a sample preparation apparatus which prepares a rocklike core sample for compressive testing in the compressive testing apparatus, via providing a throughhole in the rocklike core sample. The rocklike core sample defines a longitudinal axis and has first and second axial end, and the throughhole extends between a first opening at the first axial end and a second opening at the second axial end, the first opening and the second opening being dimensioned differently. The compressive testing apparatus is configured to: mount the rocklike core sample; and perform a compressive test on the rocklike core sample, the compressive test including compression in an axial direction parallel to the longitudinal axis and in a radial direction with respect to the longitudinal axis.

In one aspect, embodiments disclosed herein relate to a method including preparing a rock core sample for compressive testing, the rock core sample defining a longitudinal axis and having first and second axial ends. Preparing the rock core sample includes drilling a throughhole in the rock core sample, the throughhole extending between a first opening at the first axial end and a second opening at the second axial end. The throughhole includes: a first portion, cylindrical in shape, extending from the first opening; and a second portion, frustoconical in shape, extending from the first portion to the second opening; wherein the second opening has a smaller diameter than the first opening. The rock core sample is mounted in a triaxial testing apparatus, and a compressive test is performed on the rock core sample in the triaxial testing apparatus. The compressive test includes compression in an axial direction parallel to the longitudinal axis and in a radial direction with respect to the longitudinal axis.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

FIGS. 5A-5J graphically illustrate working examples of nine shapes for simulating the bottom hole geometry of wellbore in a rocklike core sample, in accordance with various embodiments.

DETAILED DESCRIPTION

Figure 1A:
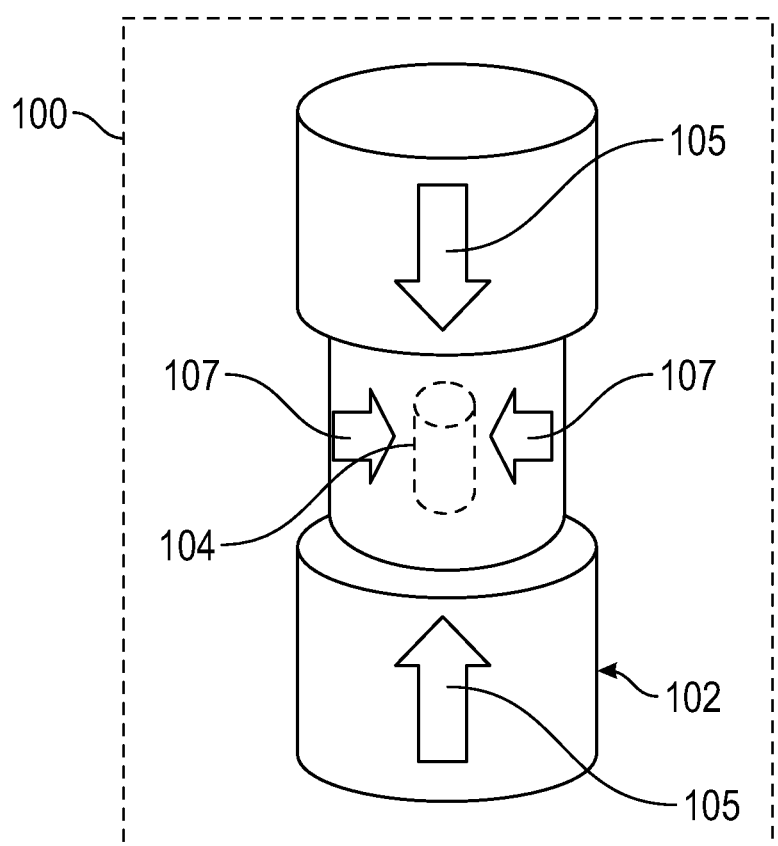
FIG. 1A schematically illustrates, in an elevational isometric view, components of a triaxial testing apparatus, in accordance with one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Turning now to the figures, to facilitate easier reference when describing FIGS. 1A through 6, reference numerals may be advanced by a multiple of 100 in indicating a similar or analogous component or element among FIGS. 1A-6.

In accordance with one or more embodiments, FIG. 1A schematically illustrates components of a triaxial testing apparatus 100. As shown, the testing apparatus 100 may include a triaxial testing cell 102 within which a cylindrical rock sample (or rock core sample) 104 is mounted, and otherwise may be embodied by a triaxial load frame. As generally known, the cylindrical rock core sample 104, once mounted, may be subjected to compressive axial and radial forces, as shown via the arrows 105 (axial) and 107 (radial). The axial and radial forces (105 and 107) can be applied in any of a variety of manners, e.g., via pressurized hydraulic fluid applied within a confined volume (e.g., in a manner described below with respect to FIG. 1B). Alternatively, the axial forces 105 can be applied by a piston or screw jack, at either or both axial ends of the sample 104.

Figure 1B:
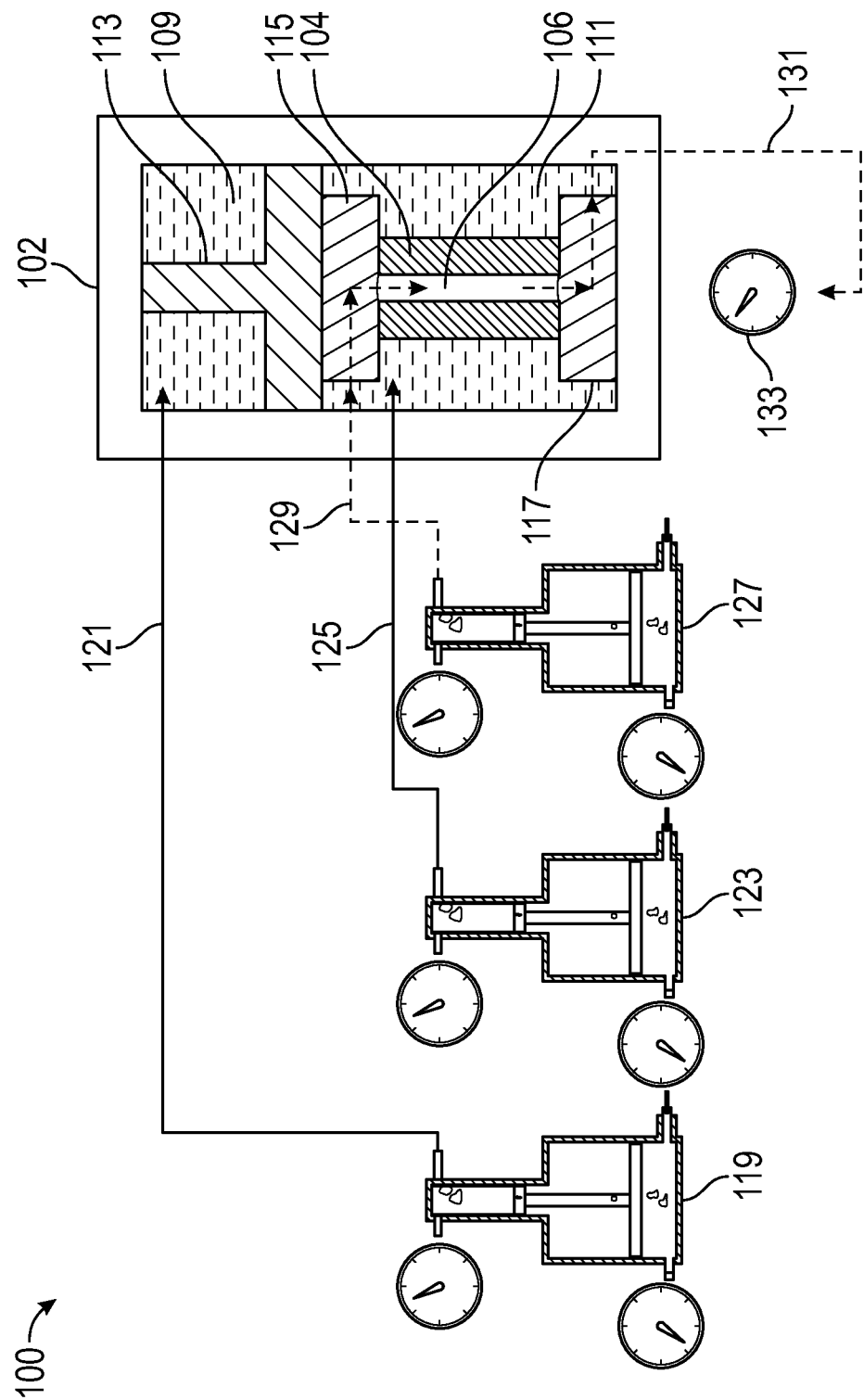
FIG. 1B schematically illustrates, in partial cross-section, a detailed elevational view of a triaxial testing apparatus in accordance with one or more embodiments.

FIG. 1B schematically illustrates, in partial cross-section, a detailed elevational view of a triaxial testing apparatus in accordance with one or more embodiments. It should be understood that this merely represents an illustrative working example of a compressive testing apparatus that can perform a compressive test on a rocklike core sample. Components shown in FIG. 1B may coincide with analogous components shown in FIG. 1A, thus continued reference may be made to both FIGS. 1A and 1B simultaneously.

As shown, in accordance with one or more embodiments, apparatus 100 includes triaxial testing cell 102 in the form of a confining vessel, for holding pressurized fluid in a first annular chamber 109 and a second annular chamber 111 to act, respectively, in an axial direction (105 in FIG. 1A) and a radial direction (107 in FIG. 1A) with respect to core sample 104. An axial piston 113 may be displaceable along the axial direction, and a lower portion thereof may be in face contact with an upper sample holder 115. Upper sample holder 115 may be in the form of a block with a passage or line therethrough for admitting pressurized fluid (e.g., liquid or air) in a manner described below. A lower sample holder 117 is also provided to cooperate with the upper sample holder 115 in axially fixing the core sample 104 for compressive testing, and may also be provided with a passage therethrough to act in a manner described below.

In accordance with one or more embodiments, an axial pressure intensifier 119 is in fluid communication with first annular chamber 109 via a line 121 to admit pressurized fluid (e.g., hydraulic oil) into the chamber 109 and control a compressive force applied by the axial piston 113, in an axially downward direction, to the sample holder 115 and thus to the core sample 104. Additionally, a confining pressure (or radial pressure) intensifier 123 is in fluid communication with second annular chamber 111 via line 125 to admit pressurized fluid (e.g., hydraulic oil) into the chamber 111 and control a compressive force applied in a radial direction to the core sample 104.

In accordance with one or more embodiments, a pore pressure intensifier 127 is in fluid communication with a throughhole 106 of core sample 104 via a line 129 which is directed through upper sample holder 115. An additional line 131 initiating in lower sample holder 117 is also in fluid communication with throughhole 106 and leads away to a downstream pressure gauge 133. The pore pressure intensifier 127 may thereby be configured to admit pressurized air into the throughhole 106 and, in concert with downstream gauge 133, control the pore pressure applied by the pressurized air within throughhole 106. In accordance with a working example, the pore pressure within throughhole 106 may be controlled to be the same as ambient or atmospheric pressure.

Figure 2:
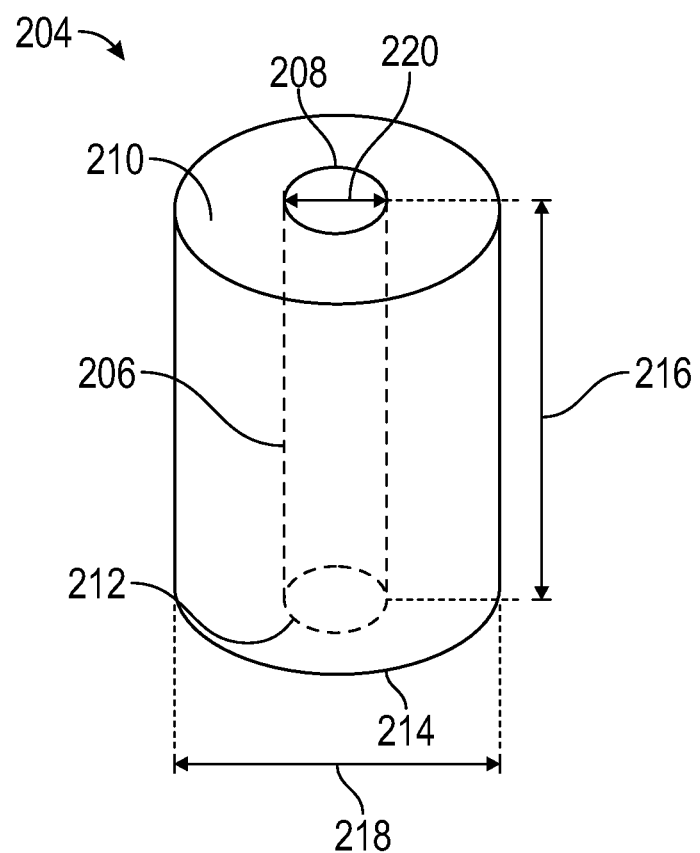
FIG. 2 illustrates, in an elevational isometric view, a conventional rock sample prepared for TWC testing.

FIG. 2 illustrates, in an elevational isometric view, a conventional rock sample 204 prepared for TWC testing, and which may be tested in a triaxial testing apparatus such as those described and illustrated with respect to FIGS. 1A and 1B. As shown, rock sample 204 is generally cylindrical in shape and includes a cylindrical throughhole 206 oriented along an axial direction, that is, coaxially with respect to a central longitudinal axis A of the sample 204. Typically, the throughhole 206 is drilled through the sample 204, and extends from a first opening 208 at a first axial end 210 of sample 204 to a second opening 212 at a second axial end 214. By way of an illustrative example, the sample 204 and throughhole 206 alike may have an axial length 216 of between about 1.5" and about 4.0", and the sample 204 may have an outer diameter 218 of about 1.5". The throughhole 206 may have an inner diameter 220 of about 0.5". With the throughhole 206 present, sample 204 can be loaded in a triaxial testing apparatus to simulate loading conditions at a wellbore under downhole stresses. Thus, this can help determine quantitatively the compressive or shear stresses that may cause production of sand in a wellbore, or that may lead to deformation or even structural failure in a wellbore casing.

Generally, for conventional TWC testing, the sample 204 is placed in a sleeve or sheath to forestall the entry of fluid into the sample 204 (e.g., pressurized fluid for causing radial compression forces as indicated at 107 in FIG. 1A). The throughhole 206 may remain at atmospheric pressure while compressive axial and radial forces are applied as noted. Essentially any appropriate measurement instruments may be used to measure deformation or strain (such as one or more radial strain gauges). Failure may occur initially in or along the inner cylindrical wall defining the throughhole 206, and any related pressure drops may be measured and recorded. The sample 204 may also then be removed from the triaxial testing apparatus and examined for any breakouts, irregularities or structural failures.

Figure 3:
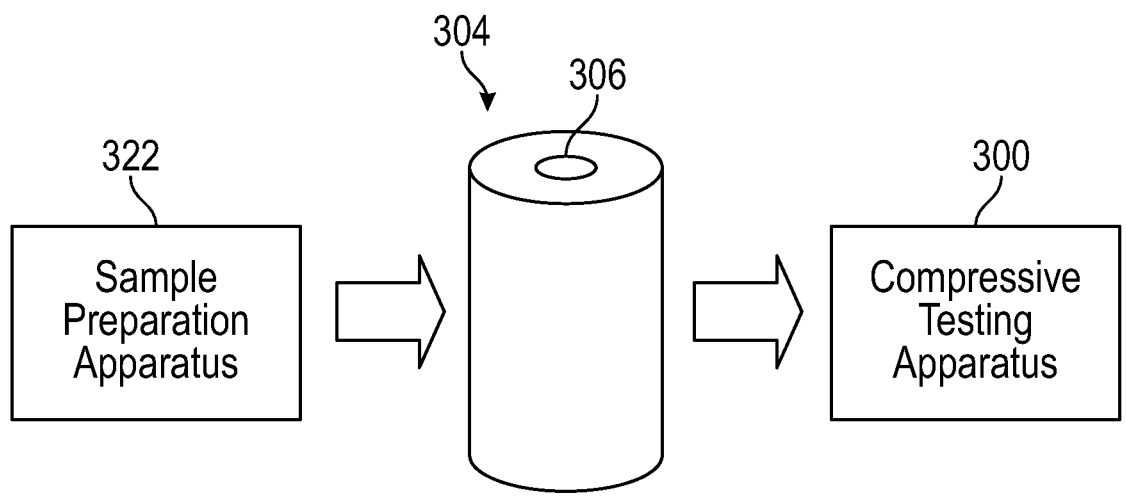
FIG. 3 schematically illustrates an experimental setup in accordance with one or more embodiments.

In accordance with one or more embodiments, an experimental setup includes a sample preparation apparatus 322 and a compressive testing apparatus 300 as shown in FIG. 3. The sample preparation apparatus 322 may provide a throughhole in a rocklike core sample 304. The rocklike core sample 304 may be formed from rock, from a synthetic material which simulates rock, or from another suitable material. Suitable synthetic materials may include (by way of non-restrictive example) Plaster of Paris, Hydrostone, cement, other synthetic materials, or a mixture of different synthetic materials. Generally, "rocklike" can be understood herein as referring to those materials, including actual rock, that can readily and effectively simulate the performance of a predetermined rock or rock type when tested in a compressive testing apparatus as described herein. The compressive testing apparatus 300 may be a triaxial testing apparatus such as one of those discussed with respect to FIGS. 1A and 1B, and configured to perform a compressive test on the rocklike core sample via compression in an axial direction and in a radial direction.

In accordance with one or more embodiments, the rocklike core sample 304 may be prepared, via sample preparation apparatus 322, in a manner to better simulate the bottomhole geometry of a wellbore, as may be affected by a drill bit for drilling a wellbore (e.g., a cone-shaped drill bit). Thus, the throughhole 306 in rocklike core sample 304 can be shaped and configured to help simulate more accurately the effect of a wellbore drill bit on wellbore stability. In this manner, a compressive test (such as a triaxial test as discussed herein) can simulate more accurately a stress distribution and evolution of breakout growth in a region of rock adjacent to a drilled wellbore.

As such, in accordance with one or more embodiments, the sample preparation apparatus 322 may include one or more drills for drilling the throughhole 306 in sample 304, whether the sample 304 is a rock sample or is formed from another material. An initial cylindrical shape of the sample 304 may thus be provided (e.g., via a coring machine), to then be drilled to form throughhole 306 and to impart an internal shape for the latter with characteristics as discussed more fully below.

Alternatively, in accordance with one or more embodiments, sample preparation apparatus 322 may be configured to form rocklike core sample 304 from a synthetic material, and provide the throughhole 306 as well, via a molding process. Here, a shape corresponding to a specific bottomhole shape of interest can be precision-cast in a mold, especially in the case of simulating bottomhole shapes that may be difficult to create via relatively small drill bits. Such synthetic material can also be controlled or configured to incorporate specific properties to simulate a specific formation of interest (e.g. brittle or ductile formations). As an alternative, a rocklike core sample 304 formed from a synthetic material, or other material substituting for porous rock, can be created via a great range of other suitable methods such as 3-dimensional (3D) printing.

Figure 4:
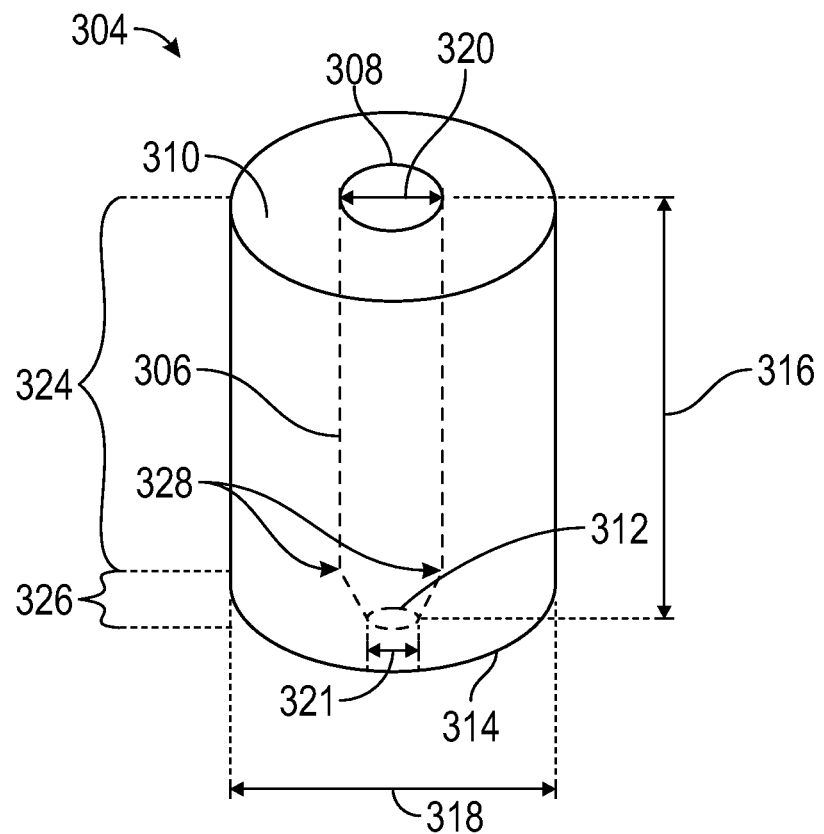
FIG. 4 illustrates, in an elevational isometric view, a working example of a prepared rocklike core sample in accordance with one or more embodiments.

FIG. 4 illustrates, in an elevational isometric view, a working example of a prepared rocklike core sample 304 in accordance with one or more embodiments. Generally, throughhole 306 of the rocklike core sample 304 may be dimensioned such that the second opening 312, at second axial end 314 of sample 304, has a smaller area than the first opening 308 at the first axial end 310. While this can be embodied in a great variety of ways, this generally can result in a better simulation of downhole conditions when sample 304 is loaded in a compressive testing apparatus, as compared to the case of a purely cylindrical throughhole (as shown in FIG. 2). In accordance with the present working example, each of the first and second openings 308, 312, defines a diameter (320 and 321, respectively), and the diameter 321 of second opening 312 is smaller than the diameter 320 of first opening 308.

In accordance with one or more embodiments, in the working example illustrated in FIG. 4, the throughhole 306 includes two axial portions 324 and 326. The first portion 324, cylindrical in shape, extends from the first opening 308, and the second portion 326, frustoconical in shape, extends from the first portion 324 (at a circular transition region 328) to the second opening 312. The frustoconical shape of second portion 326 may be formed via a cone-shaped drill bit if the throughhole 306 is drilled, or may be formed as part of a molding process, or other process, for forming sample 304.

As shown, in accordance with one or more embodiments, the resulting throughhole 306 will be defined by a sloped inner profile at its lower axial end (in second portion 326), and its exit diameter (at the second axial end 314 of the core sample 304, at second opening 312) will be smaller than its entry diameter (at the first axial end 310 of core sample 304, at first opening 308). Thus, in accordance with a working example as shown in FIG. 4, By way of sample dimensions in a working example in accordance with one or more embodiments, the diameter 320 of the first opening 308 may be about 0.5 inch, while the diameter 321 of the second opening 312 may be about 0.25 inch. The second portion 326 may define a cone angle of between about 30 degrees and about 60 degrees and, by way of an illustrative and non-restrictive example, may be about 45 degrees. Otherwise, the sample 304 and throughhole 306 alike may have a total axial length 316 of between about 1.5" and about 4.0", and the sample 304 may have an outer diameter 318 of about 1.5".

Generally, in accordance with one or more embodiments, it should be appreciated that essentially any cone angle of less than 90 degrees will provide an advantage of increasing a likelihood of structural failure in the sample 304, for the purpose of providing a better simulation of a "real-world" bottomhole environment or geometry as discussed. At the same time, a moderate cone angle that is between about 30 degrees and about 60 degrees can be of benefit in a scenario where the exact geometry of a "real-world" downhole drill bit may not be known in advance and an objective may involve simulating the general effect of such a downhole drill bit on a bottomhole environment. Thus a cone angle of about 45 degrees can be particularly beneficial in that regard.

Generally, in accordance with one or more embodiments, a rocklike core sample 304 may be tested in a compressive testing apparatus, such as that indicated at 300 in FIG. 3, wherein the first opening 308 and second opening 312 are dimensioned differently. Once tested, the rocklike core sample 304 can be removed from the compressive testing apparatus and examined for breakouts, irregularities or structural failures, based on the first opening 308 and the second opening 312 being dimensioned differently, such that the bottomhole geometry of a wellbore is more effectively simulated than in the case of a purely cylindrical throughhole.

Figure 5A:
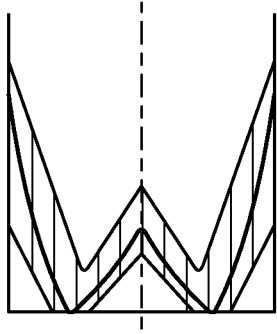
Figure 5B:
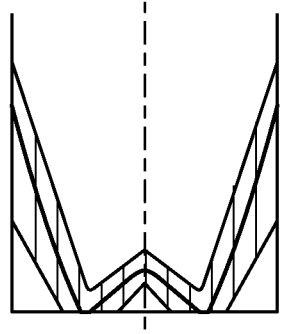
Figure 5C:
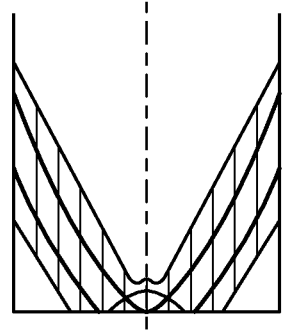
Figure 5D:
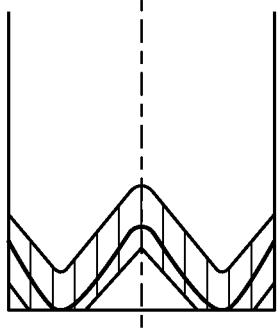
Figure 5E:
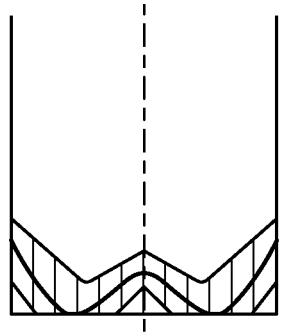
Figure 5F:
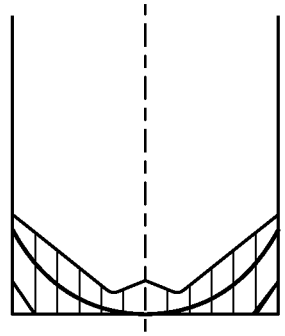
Figure 5G:
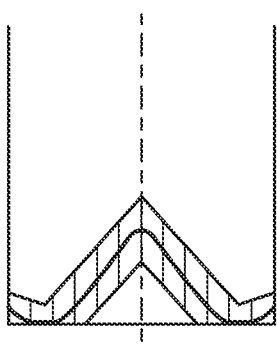
Figure 5H:
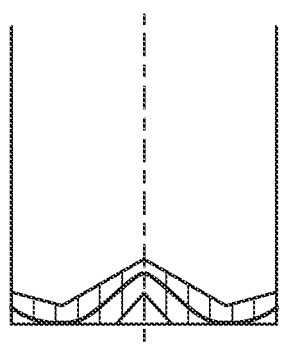
Figure 5J:
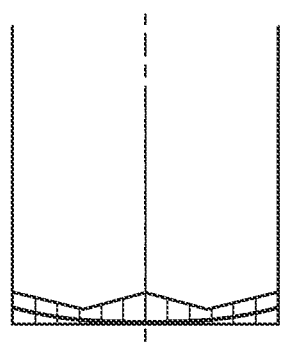

As the working example of FIG. 4 relates to a sample 304 which simulates the effect of a conical drill bit in drilling a wellbore, it should be appreciated that a great variety of possible shapes can be simulated for the bottomhole geometry of a wellbore in accordance with one or more embodiments. Thus, FIGS. 5A-5J graphically illustrate nine such possible shapes, corresponding to a range of profiles for cone- or parabolic-shaped drill bits that may be used in wellbore drilling. The profiles shown are adopted from the IADC (International Association of Drilling Contractors) code, but it should also be understood that a great variety of other possible shapes are still conceivable. Thus, analogously shaped drill bits may be used to drill a throughhole 306 as shown in FIG. 3, or suitable molding (or other) processes may be used to effect similar shapes. FIGS. 5A, 5B and 5C illustrate "long tapers", including a "deep cone", "medium cone" and "shallow parabolic cone", respectively. FIGS. 5D, 5E and 5F illustrate "medium tapers", including a "deep cone", "medium cone" (or "double cone") and "shallow rounded cone", respectively. FIGS. 5G, 5H and 5J illustrate "short tapers", including a "deep cone", "medium cone" and "shallow" or "flat" cone, respectively. FIGS. 5A-5J may be understood to provide an accurate representation of the angles and other dimensions involved.

Generally, in accordance with one or more embodiments, it has been found that a generally cone-shaped drill bit for drilling a throughhole in a core sample results in a better simulation (through TWC testing) of weak points in a rock layer that typically may be encountered or promoted as a drill bit progresses downhole in a "real-world" setting. Particularly, it is recognized that a downhole drilling process typically introduces some damage to the rock mass around the wellbore, and below the wellbore bottom. The damage will be affected by the penetrating and rotating speeds of the downhole drill bit; consequently, the integrity and stability of the rock mass will typically be influenced.

In this regard, it has been found that in TWC experiments run with core samples having merely cylindrical throughholes, material stresses acting in the region of a downhole drill bit are greatly underestimated. By forming a core sample throughhole with a generally conical internal profile at its lower end (whether formed by drilling or via a mold), as broadly contemplated herein, TWC experiments then end up taking into account such factors such as dilation angle and unit weight of rock material acting on a slope, thus significantly enhancing the accuracy of the experiments. In turn, this can greatly enhance the accuracy of a wellbore stability model such as a Mohr-Coulomb model.

Figure 6:
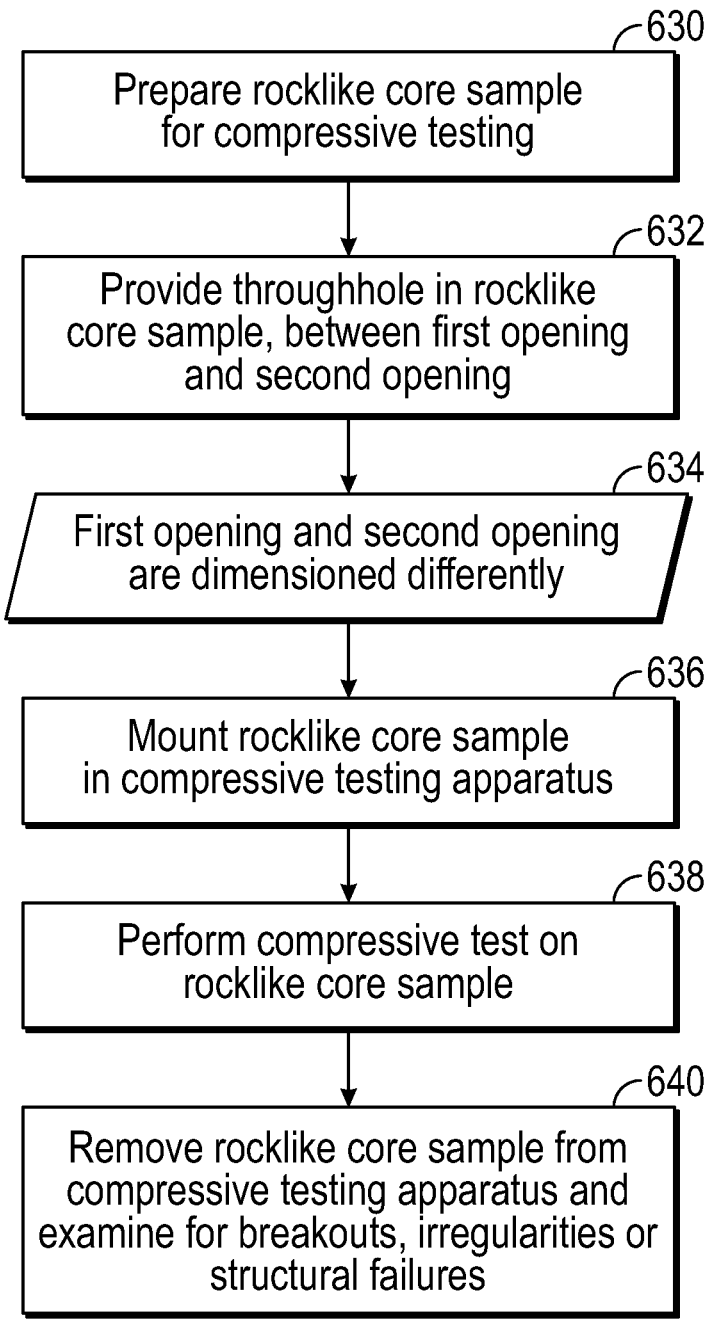
FIG. 6 shows a flowchart of a method in accordance with one or more embodiments.

FIG. 6 shows a flowchart of a method, as a general overview of steps which may be carried out in accordance with one or more embodiments described or contemplated herein.

As such, in accordance with one or more embodiments, a rocklike core sample is prepared for compressive testing, the rocklike core sample defining a longitudinal axis and having first and second axial ends (630). This can correspond to the sample 304 described and illustrated with respect to FIGS. 3 and 4. Preparing the rocklike core sample includes providing a throughhole in the rocklike core sample, the throughhole extending between a first opening at the first axial end and a second opening at the second axial end (632). Also, the first opening and the second opening are dimensioned differently (634). By way of illustrative example, the throughhole can correspond to that indicated at 306 in FIGS. 3 and 4, with openings 308 and 312. By way of additional example, a corresponding rocklike core sample can be prepared via a sample preparation apparatus 322 as described with respect to FIG. 3.

In accordance with one or more embodiments, the rocklike core sample is mounted in a compressive testing apparatus (636). A compressive test is performed on the rocklike core sample in the compressive testing apparatus, the compressive test including compression in an axial direction parallel to the longitudinal axis and in a radial direction with respect to the longitudinal axis (638). By way of illustrative example, the compressive testing apparatus can correspond to those described and illustrated with respect to FIGS. 1A and 1B, to perform a compressive test as there described. The rocklike core sample is removed from the compressive testing apparatus and examined for breakouts, irregularities or structural failures, based on the first opening and the second opening being dimensioned differently (640). This can be appreciated, by way of illustrative example, in connection with the rocklike core sample 304 discussed with respect to FIGS. 3 and 4, especially inasmuch as the bottomhole geometry of a wellbore is more effectively simulated than in the case of a purely cylindrical throughhole.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed:

1. A method comprising:
preparing a rocklike core sample for compressive testing, the rocklike core sample defining a longitudinal axis and having first and second axial ends;
wherein preparing the rocklike core sample includes providing a throughhole in the rocklike core sample, the throughhole extending between a first opening at the first axial end and a second opening at the second axial end;
the first opening and the second opening being dimensioned differently;
mounting the rocklike core sample in a compressive testing apparatus; and
performing a compressive test on the rocklike core sample in the compressive testing apparatus, the compressive test including compression in an axial direction parallel to the longitudinal axis and in a radial direction with respect to the longitudinal axis.

2. The method according to claim 1, wherein the compressive testing apparatus is a triaxial testing apparatus and the compressive test is a thick wall cylinder test.

3. The method according to claim 1, wherein the second opening has a smaller area than the first opening.

4. The method according to claim 3, wherein the second opening has a smaller diameter than the first opening.

5. The method according to claim 4, wherein the throughhole includes:
a first portion, cylindrical in shape, extending from the first opening; and
a second portion, frustoconical in shape, extending from the first portion to the second opening.

6. The method according to claim 5, wherein the second portion defines a cone angle of between about 30 degrees and about 60 degrees.

7. The method according to claim 6, wherein the cone angle is about 45 degrees.

8. The method according to claim 3, wherein the rocklike core sample is generally cylindrical in shape.

9. The method according to claim 1, wherein providing a throughhole comprises drilling a throughhole through the rocklike core sample.

10. The method according to claim 1, wherein the rocklike core sample is a rock sample.

11. The method according to claim 1, wherein the rocklike core sample is formed from a synthetic material.

12. The method according to claim 11, wherein:
via a molding process, the synthetic material is molded to form the rocklike core sample; and
providing a throughhole comprises forming the throughhole via the molding process.

13. A system comprising:
a compressive testing apparatus; and
a sample preparation apparatus which prepares a rocklike core sample for compressive testing in the compressive testing apparatus, via providing a throughhole in the rocklike core sample;
wherein the rocklike core sample defines a longitudinal axis and has first and second axial end, and the throughhole extends between a first opening at the first axial end and a second opening at the second axial end, the first opening and the second opening being dimensioned differently;
the compressive testing apparatus being configured to:
mount the rocklike core sample; and
perform a compressive test on the rocklike core sample, the compressive test including compression in an axial direction parallel to the longitudinal axis and in a radial direction with respect to the longitudinal axis.

14. The system according to claim 13, wherein the compressive testing apparatus is a triaxial testing apparatus and the compressive test is a thick wall cylinder test.

15. The system according to claim 13, wherein the second opening has a smaller area than the first opening.

16. The system according to claim 15, wherein the throughhole includes:
   a first portion, cylindrical in shape, extending from the first opening; and
   a second portion, frustoconical in shape, extending from the first portion to the second opening.

17. The system according to claim 13, wherein the sample preparation apparatus provides the throughhole via drilling a throughhole through the rocklike core sample.

18. The system according to claim 13, wherein the rocklike core sample is a rock sample.

19. The system according to claim 13, wherein:
   the rocklike core sample is formed from a synthetic material; and
   the sample preparation apparatus:
   forms the rocklike core sample via a molding process; and
   forms the throughhole via the molding process.

20. A method comprising:
preparing a rock core sample for compressive testing, the rock core sample defining a longitudinal axis and having first and second axial ends;
wherein preparing the rock core sample includes drilling a throughhole in the rock core sample, the throughhole extending between a first opening at the first axial end and a second opening at the second axial end;
wherein the throughhole includes:
   a first portion, cylindrical in shape, extending from the first opening; and
   a second portion, frustoconical in shape, extending from the first portion to the second opening;
wherein the second opening has a smaller diameter than the first opening;
mounting the rock core sample in a triaxial testing apparatus; and
performing a compressive test on the rock core sample in the triaxial testing apparatus, the compressive test including compression in an axial direction parallel to the longitudinal axis and in a radial direction with respect to the longitudinal axis.

* * * * *